United States Patent
Noguchi

(10) Patent No.: US 6,699,513 B2
(45) Date of Patent: Mar. 2, 2004

(54) DRUGS AND HEALTH FOODS

(76) Inventor: Shin-ichi Noguchi, 13-1, Gakuen 6-chome, Sanda-shi, Hyogo (JP), 669-1337

(*) Notice: Subject to any disclaimer, the term of this patent is extended or adjusted under 35 U.S.C. 154(b) by 42 days.

(21) Appl. No.: 09/979,781

(22) PCT Filed: Sep. 6, 2001

(86) PCT No.: PCT/JP01/07754

§ 371 (c)(1),
(2), (4) Date: Nov. 27, 2001

(87) PCT Pub. No.: WO02/20029

PCT Pub. Date: Mar. 14, 2002

(65) Prior Publication Data

US 2003/0082251 A1 May 1, 2003

(30) Foreign Application Priority Data

Sep. 8, 2000 (JP) ........................................ 2000-273693

(51) Int. Cl.$^7$ .......................... A01N 65/00; A61K 35/78
(52) U.S. Cl. ........................................ 424/769; 424/776
(58) Field of Search ................................. 424/769, 776, 424/764

(56) References Cited

FOREIGN PATENT DOCUMENTS

| JP | 1995-165589 | * | 6/1995 |
| JP | 2002-225386 | * | 8/2000 |

* cited by examiner

Primary Examiner—Herbert J. Lilling
(74) Attorney, Agent, or Firm—Wenderoth, Lind & Ponack, L.L.P.

(57) ABSTRACT

The present invention is the medicine comprising the pulverized product of the ume seeds or its processed product, and thereby can provide a valuable way of using of the ume seeds, which were discarded as useless materials.

9 Claims, 2 Drawing Sheets

DRUGS AND HEALTH FOODS

TECHNICAL FIELD

This invention relates to a medicine or a pharmaceutical composition, which contains the pulverized product of the seed of ume fruit (Japanese apricots) or its processed product.

BACKGROUND ART

The ume trees, the original home of which is considered to be in the central or southern regions of China, have features that they are in blossom leading other trees in the early spring and emit a nice smell. From old times the ume trees with flowers have been used for admiration and the ume fruits are for food. The ume trees have mainly been cultivated in the eastern Asia, and it does not seem to have been introduced into England and America.

The pickled umes made of ume fruits have been one of the important preservable foods from old times in Japan. And the ume wine, which is also produced by utilizing ume fruits as the raw material, has been highly esteemed as one of the table luxuries. Formerly, the pickled umes and ume wine had been produced at each home, and the seeds of the pickled umes had been discarded at each home. And, after the sarcocarp part of the ume fruits used for production of the ume wine was eaten, the remaining seeds had also been discarded.

The seeds of ume fruits can not usually be eaten because of their very hard outer core. The sarcocarp part of the pickled umes was eaten, and the seeds of them were discarded. Recently, the pickled umes are manufactured in factories. As for some portion of the ume fruits harvested, after taking out the seeds, the sarcocarp part is processed to yield products such as "ume juice" and "ume sarcocarp extract", and the like, which are on the market. In this case the seeds of the ume fruits have also been discarded. The ume wine has also been manufactured by the use of ume fruits as a raw material, and, after yielding the ume wine, the ume fruits were separated from the ume wine, then the ume fruits themselves have been discarded.

Recently, especially in the advanced countries, foods go around sufficiently, and men and women are both predisposed to be obese due to supernutrition. In addition, due to insufficient exercise, they have a low metabolic rate, and, as a result, nutrients of foods taken could not be sufficiently carried to the cells. Then, wastes can be hardly excreted from the body, and these result in prevalence of various types of diseases, for example, diseases incidental to civilization, adult disease and life-style related disease.

Various western medicines have been used as therapeutics for these diseases. Western medicines are requested to clarify the mechanisms of action by which their effectiveness can be rationally explained, so a huge fund is needed to develop new western medicines. Further, western medicines are not totally free of toxicity or side effects.

On the other hand, herb medicines have been used mainly on the basis of an old tradition, and although the mechanisms of action for the effectiveness are unclear in many cases, there seems no trend of declining in their popularity, because of their mild therapeutic actions. The ume sarcocarp extract mentioned above is one of such traditional medicines in Japan.

DISCLOSURE OF INVENTION

It is an object of the present invention to provide a useful medicine or a pharmaceutical composition for prevention of or treatment for various diseases in humans or animals including diseases, for example, diseases incidental to civilization, adult diseases and life-style related diseases substantially without side effects or toxicity, which can easily be manufactured at a low cost, and are easily available at home without indication of a doctor or prescription.

Generally speaking, seeds of plants are rich in nutrients, and useful as foodstuffs or health foods. The present inventor has hitherto been interested in this point, and has studied to find how to utilize the seeds of ume fruits effectively, which have been discarded so far, as mentioned above. Then, the inventor made trial products of new foods obtained by pulverizing the seeds of ume fruits after cleansing and drying. The trial products showed a prominent beneficial effect in some subjects incidentally having suffered from gastric hyperacidity among the people who took it. This finding was the first unforeseen discovery. Soon after, among the people who took the new foods, some ones had an experience of being full of vitality or spirits in their daily life, or of disappearance of spots in the skin. Thus, the information of the new health foods of the present invention was passed from mouth to mouth, and as a result, many people rushed to the inventor and had a hope of trying to take the new foods. There were several subjects having suffered from various diseases among the people who took the new foods of the present invention. Such people had an experience of improvement of the diseases after taking the foods of the present invention, which was judged by themselves or doctors, and the present inventor recorded the reports from them. As a result, it was unexpectedly and surprisingly found that, as shown in the description of the examples below, the pulverized product of the seeds of ume fruits (hereinafter referred to simply as the ume seeds) or its processed product (for example, the extracted product from the pulverized product and so on) was effective in improving or curing the symptoms such as gastric ulcer, gastric dilatation, gastric hyperacidity, stomachache, gastrospasm, heartburn, constipation, duodenal ulcer, herpes, stiffness of the shoulders, menorrhalgia, menoxenia, poor circulation, asthma, infantile asthma, heart diseases, feebleness, hangover, insomnia, cystitis, rheumatism, menopausal syndrome, hepatitis C, liver diseases, pollinosis, dermatosis, atopic dermatitis, leukemia, cancer, arteriosclerosis, hypertension, neurosis, kann-no mushi (a worm which is supposed to cause irascibility in children), bed-wetting, spots in the skin, hyperlipidemia, diabetes mellitus, prostatomegaly, gout, obesity, fatty liver, nausea, arrhythmias, myocardial infarction, cardiac diseases, allergic diseases, various types of polyps, Basedow's disease, hypothyroidism, or headache, and so on. The inventor expects that this invention will be approved as a medicine by the Welfare Ministry in every country in the world in the near future, and will contribute to the promotion of happiness of the people.

Thus the present invention relates to:

(1) A medicine, which comprises the pulverized product of ume seed or its processed product, (2) A medicine as described in (1) above, wherein the medicine is a preventive or therapeutic agent for gastric ulcer, gastric dilatation, gastric hyperacidity, stomachache, gastrospasm, heartburn, constipation, duodenal ulcer, herpes, stiffness of the shoulders, menorrhalgia, menoxenia, poor circulation, asthma, infantile asthma, heart diseases, feebleness, hangover, insomnia, cystitis, rheumatism, menopausal syndrome, hepatitis C, liver diseases, pollinosis, dermatosis, atopic dermatitis, leukemia, cancer, arteriosclerosis, hypertension, neurosis, kann-no mushi (a worm which is supposed in Japan to cause irascibility in children), bed-wetting, spots in the skin, hyperlipidemia, diabetes mellitus, prostatomegaly, gout, obesity, fatty liver, nausea, arrhythmias, myocardial infarction, cardiac diseases, allergic diseases, various types of polyps, Basedow's disease, hypothyroidism, or headache or the like.

(3) A medicine as described in (1) above, wherein the medicine is a preventive or therapeutic agent for hepatitis C, leukemia, cancer, hypertension, asthma in children, gastric hyperacidity or insomnia.

(4) A medicine as described in (1) above, wherein ume seed contains at least one of the outer core, sarcocarp and embryo.

(5) A medicine as described in (1), wherein ume seed is derived from pickled ume or ume-wine ume, (6) A medicine as described in (1) above produced by the manufacturing method, which is characterized by that the pulverized product of the ume seed is obtained by pulverizing the seed derived from pickled ume or the seed derived from ume-wine ume, (7) A medicine as described in (1) above, wherein the processed product is an extracted product of the pulverized product, (8) A medicine as described in (1) above, wherein the preparation form of the medicine is powders, tablets, granules or capsules, (9) A health food or drink, which comprises the pulverized product of ume seed or its processed product,

(10) A medicine, health food or drink containing the pulverized product of the embryo of ume seed or its processed product,

(11) A pulverized product of ume seed or its processed product, which is characterized by that the pulverized product is of 100 to 900 $\mu$m in the long axis, or of 30 to 150 mesh-pass in the particle diameter.

BEST MODE FOR CARRYING OUT THE INVENTION

Figure 1:
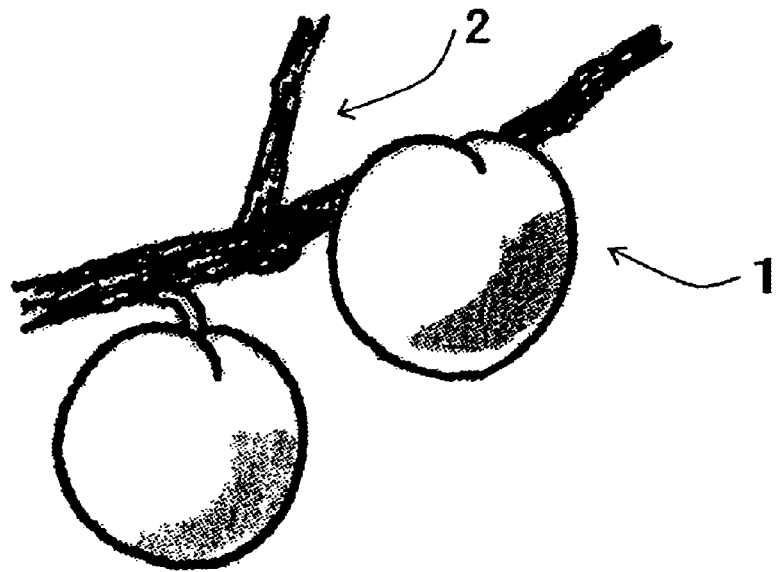
FIG. 1 shows a perspective view of an ume-tree branch with two ume fruits.

The ume, which belongs to the plum subgenus of the cherry genus of the rose family with a scientific name of Prunus Mume Sieb. et Zucc., is named Mei in Chinese, Japanese Apricot in English, Japanische Aprikose in Germany, and Prunier du Japon in French.

There are many varieties of the ume. For example, in an old Japanese book 'Kadan-chi-nishiki-shou' published in 1695, 29 varieties of Haku-bai (white-blossomed ume tree), 25 varieties of Ko-bai (red-blossomed ume tree), and 6 varieties of Zasshoku (parti-colored ume tree) are described, and the ume named Koshu-Saishou, Ryukyo-Ko-ume, Nankou, Inazumi, Shiro-Kaga, Gyoku-ei, Bungo and O-ume (grown in Wakayama prefecture) are exemplified. In this invention the ume seeds derived from any variety of the ume can be used.

In this invention, the ume seeds composed of the outer core, endocarp and embryo, which are contained in ume fruits, are used, but it does not matter if the ume seeds are attached with the exodermis (outer cover) or sarcocarp. The outer cover of ume fruits is the most outer layer, in the inner-side of which is the sarcocarp, and the seed is in the center of the sarcocarp. Therefore, in this invention, ume fruits themselves collected from ume trees can also be used as the ume seeds.

The ume seeds derived from pickled umes made of ume fruits, with or without the sarcocarp eliminated, can be used as a raw material for manufacturing the medicine of the present invention.

The ume wine is produced by using ume fruits as a raw material, and the ume fruits having used for that purpose and separated from the ume wine in the producing process of the ume wine can be used as a raw material for manufacturing the medicine of the present invention. In this case, it does not matter if the sarcocarp is eliminated or not. In the following descriptions the ume fruits after having been used for production of ume wine are referred to as the ume-wine umes.

Since methods for making pickled umes of ume fruits and for making ume wine from ume fruits have been well-established, respective methods can be used for those purposes.

In this invention, the processed goods of ume fruits such as pickled umes mentioned above, the waste materials after eating such processed goods, or the ume fruits generated as a waste material during manufacturing processed goods (for example, ume-wine umes discarded after having produced ume wine) can be used as the ume seeds for production of the medicine of the present invention. In addition, the seeds derived from unprocessed ume fruits can also be used.

In either case, it is preferable to pulverize the ume seeds after dried. The temperature for drying is about 50 to 120° C., and it is preferable to use hot air or infrared rays as a heat source. The heating time for drying is about 6 to 50 hours may be sufficient to dry them, although it can not be stated absolutely.

In order to pulverize the ume seeds, any pulverizer described below can be used, if it can pulverize the ume seeds into desired sizes, especially, a hand mill, a hammer mill, a power mill and a ball mill are preferable, and a hand mill made from ceramic is more preferable. The preferable size of the pulverized product is, with smooth corners, to the extent of being able to be swallowed smoothly, when taken by humans or animals as it is. Thus, such a size is, for example, about 2 mm or less, preferably about 0.1 to 1000 $\mu$m, more preferably about 100 to 900 $\mu$m, and most preferably about 100 to 600 $\mu$m in the long axis of particles of the pulverized product. Here, the long axis means the longest particle diameter of the particles. The said long axis can be measured with, for example, a microscope, preferably with a microscope with a built-in ruler.

In addition, the preferable size of the pulverized product is about 30 to 150 mesh-pass, namely, the size of being able to be passed through a filter of about 30 to 150 mesh.

The followings are descriptions of the preferred modes of carrying out the present invention.

According to the present invention, useful medicines for prevention of or treatment for diseases including diseases incidental to civilization, adult disease, or life-style related disease can be obtained from the seeds of pickled umes or ume-wine umes, which were previously industrial waste. The seeds of pickled umes in pickled-ume factories and ume-wine umes in ume-wine factories are generated in large quantity. The seeds derived from pickled umes and the seeds derived from ume-wine umes are cleansed and removed extraneous matters such as the dusts attached to the outer core. It does not matter if the sarcocarp adhered to the seeds is left behind, because it is generally not harmful. The cleansed seeds, after dried at about 60° C., are pulverized with a pulverizer. The pulverized product of the present invention can easily be manufactured through pulverization of the ume seeds. The ume seeds are composed of the hard outer core, endocarp and nut-like embryo, and the outer core, generally together with the endocarp and embryo, is pulverized to particles with smooth corners, to the extent of the size being able to be swallowed smoothly, preferably of about 100 to 900 μm, or of about 30 to 150 mesh-pass. The endocarp and embryo can easily be pulverized, when the outer core is pulverized. The pulverized product manufactured in that way is usually in the form of powders or granules with the size mentioned above. The pulverized product can be taken as it is, or the product is further pulverized into fine particles with about 1 to 100 μm in the long axis. The pulverized product mentioned above can be supplied in the form of powders as it is, or can be processed to be a form of tablets, granules, or is capsules and so on.

Figure 2:
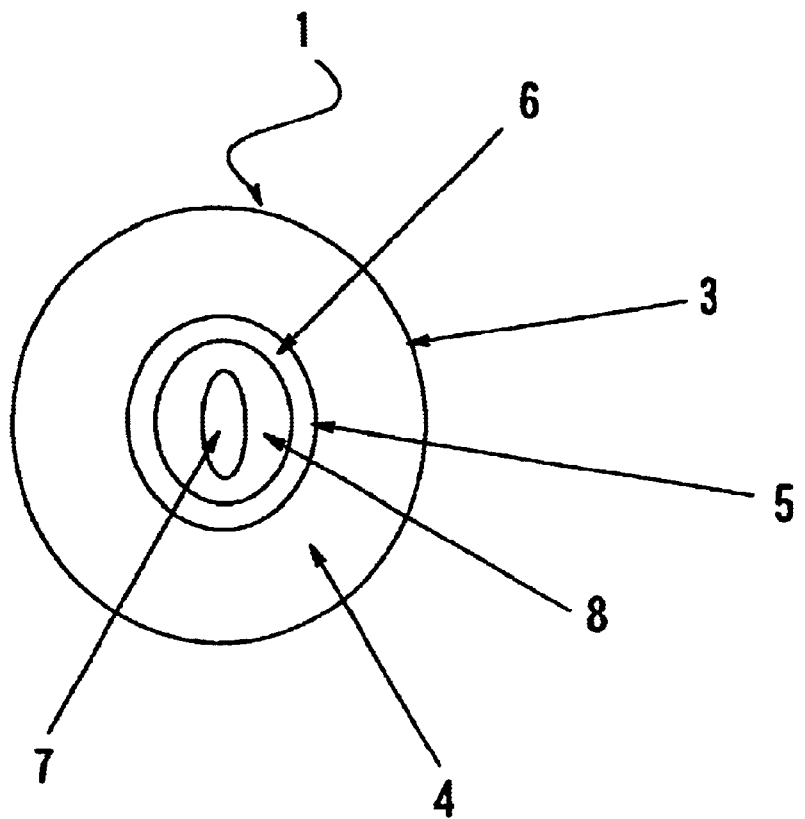
FIG. 2 shows a cross-sectional view of a ume fruit.
Figure 3:
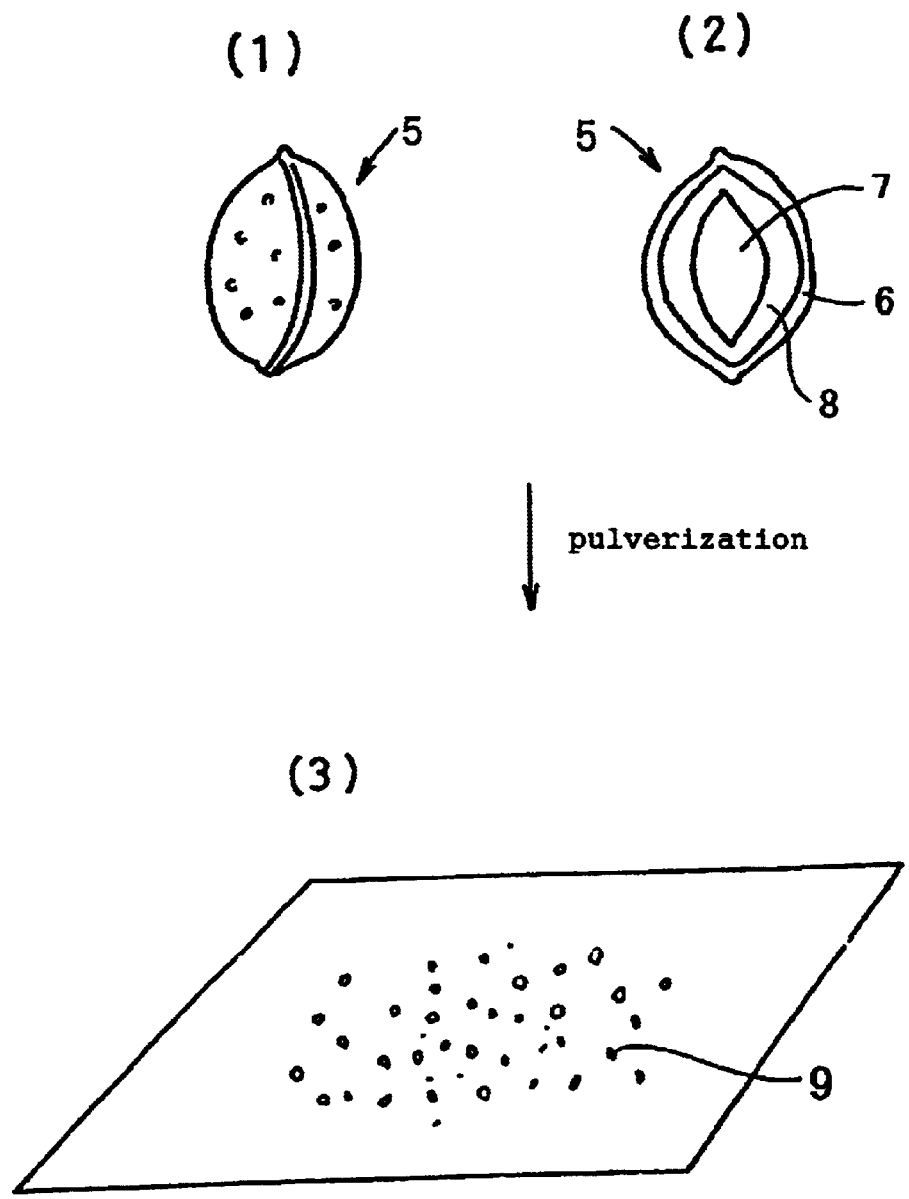
FIG. 3 shows (1) a perspective view of an ume seed, (2) a cross-sectional view of (1), and (3) a perspective view of the pulverized product 9 of the ume seeds.

FIG. 1 shows a perspective view of a branch with two ume fruits, and 1 denotes the ume fruit and 2 shows a branch of the ume tree. FIG. 2 shows a cross-sectional view of an ume fruit 1, and the ume seed 5 is covered with the outer cover 3 and sarcocarp 4. FIG. 3(1) shows a perspective view of an ume seed 5, and FIG. 3(2) shows a cross-sectional view of a ume seed 5. The seed 5 is composed of the hard outer core 6, endocarp 8 and embryo 7, and, thus, the embryo 7 is protected by the outer core 6 and endocarp 8. In this mode of the present example, the seeds (2.5 to 4 g in weight) from pickled umes of the O-ume variety produced in Wakayama prefecture were used. These seeds, after cleansed and dried, were pulverized to be of about 100 to 900 μm in the size with a pulverizer. FIG. 3(3) shows a perspective view of the pulverized product 9 of the seeds. The pulverized product 9 is used as the medicine of the present invention (hereinafter referred to as the present medicine, too).

The medicine of the present invention also includes the processed product of the pulverized product of the ume seeds, instead of the pulverized product itself of the ume seeds. Concretely, as such a processed product, an extracted material from the pulverized product can be exemplified. Concretely, as a solvent for extraction, there can be mentioned, for example, water or hydrophilic solvents like alcohols such as ethanol, or the like, steam, or a mixed solvent obtained by combining some of these solvents.

The extraction can be carried out by any known method. For example, the extract obtained by concentrating the extracted material under reduced pressure, namely, the residue can be used as a raw material for production of the medicine of the present invention. In this invention, particularly, a concentrated product of the hot water extract is preferable. For example, 500 parts by weight of the pulverized product of the ume seeds are extracted by 2000 parts by weight of hot water of about 100° C., followed by filtration, and the filtrate is concentrated under reduced pressure of about 10 mmHg to yield extract.

Further, besides being used as the medicine, the pulverized product of the ume seeds or its processed product of the present invention are useful as health foods or health drinks. For example, it can be used as a raw material for manufacturing bread, noodles or confectionery (such as crackers etc.) and so on, for example, foods manufactured by mixing the pulverized product with wheat flour are of value as health foods of bread, noodles or confectionery etc. Moreover a hot-water extract produced by subjecting the pulverized product of the ume seeds to extraction with hot water, which can be done by the similar way of producing tea or coffee, tastes good with the scent of ume fruits, and will be a drink helpful for health.

It is preferable to use the pulverized product of the ume seeds or its processed product such as the extracted product, manufactured as described above, as the medicine or health foods of the present invention. Or the pulverized product or its processed product can be used as it is as the medicine or health foods of the present invention in the form of powders or granules, tablets, capsules, pills or troches. As for the tablets mentioned above, it does not matter if they are sustained release tablets, coated tablets such as sugar-coated, entericcoated or film-coated ones, or masked ones. Further, it does not matter if the medicine, or health foods or drinks containing the pulverized product of the ume seeds or its processed product of the present invention are of the liquid preparation such as solutions, suspensions, syrups or elixirs and so on available pharmaceutically. Such medicines, or health foods or drinks can be manufactured according to the per se well-known methods or common methods used in the field of pharmaceutics or in the field of foods.

In the medicine, or health foods or drinks of the present invention, together with the pulverized product of the ume seeds or its processed product, one or more than two of additives for formulation or food additives can be added. In order to produce solid preparations such as capsules, tablets, powders, or granules and so on, the following additives can be used: for example, excipients such as lactose, glucose, sucrose, mannitol, and so on; disintegrators such as starch, sodium arginate, and so on; lubricants such as magnesium stearate, talc, and so on; binders such as polyvinyl alcohol, hydroxypropylcellulose, gelatin, and so on; surfactants such as fatty acid esters, and so on; plasticizers such as glycerin and so on. In case that the medicine of the present invention is liquid preparation, the following additives for medicines can be used: for example, water, saccharides such as sucrose, sorbitol, fructose, and so on; glycols such as polyethyleneglycole, propylenglycole, and so on; oils such as sesame oil, olive oil, soybean oil, and so on; antiseptics such as p-hydroxybenzoic esters, and so on. Further, the capsular preparations can easily be produced by filling the commonly used capsules for medicines with powders or granules.

Further, the medicine of the present invention can be used concomitantly with other medicines or functional foods and so on. As for the foods of the present invention, the foods produced by adding the pulverized product of the ume seeds or its processed product, manufactured as mentioned above, for example, to other foods such as confectionery or drinks, and soon can be mentioned. More concretely, the pulverized product of the ume seeds in the form of powders or granules can be taken after adding to tea or milk and stirring up.

Further, the pulverized product of the ume seeds and its processed product manufactured as mentioned above can be used as a seasoning as it is. Furthermore, the pulverized product of the ume seeds or its processed product manufactured as mentioned above can be used as a seasoning after dissolving or suspending in a solvent such as water, oils and so on. Furthermore, it can be mixed with other seasonings to yield seasonings with the scent of ume fruits.

The medicine, or health foods or drinks of the present invention are effective for prevention of or treatment for various diseases. As said diseases, there can be mentioned, for example, gastric ulcer, gastric dilatation, gastric hyperacidity, stomachache, gastrospasm, heartburn, constipation, duodenal ulcer, herpes, stiffness of the shoulders, menorrhalgia, menoxenia, poor circulation, asthma, infantile asthma, heart diseases, feebleness, hangover, insomnia, cystitis, rheumatism, menopausal syndrome, hepatitis C, liver diseases, pollinosis, dermatosis, atopic dermatitis, leukemia, cancer, arteriosclerosis, hypertension, neurosis, kann-no mushi (a worm which is supposed to cause irascibility in children), bed-wetting, spots in the skin, hyperlipidemia, diabetes mellitus, prostatomegaly, gout, obesity, fatty liver, nausea, arrhythmias, myocardial infarction, cardiac diseases, allergic diseases, various types of polyps, Basedow's disease, hypothyroidism, or headache, and so on. Among them, it is especially effective for hepatitis C, leukemia, cancer, hypertension, infantile asthma, gastric hyperacidity or insomnia.

Oral doses of the medicine according to the present invention can not absolutely be defined because it depends on the symptoms, usually, preferably about 5 to 100 g/time, or more preferably about 10 to 50 g/time, 3 to 10 times a day as the pulverized product. Since the efficacy is less pronounced with doses less than about 5 g/time, the doses can be adjusted within a range of the doses mentioned above depending on the symptoms. When taking over about 100 g/time, the efficacy may be increased. Since the pickled umes and ume-wine umes are foods, no one will be addicted to the medicine of the present invention manufactured from the seeds of these foods, even when taking them everyday, and there is no side effects nor toxicity, even taking over about 100 g/time. Also, taking only once a day will be effective.

Besides, the seeds from pickled umes or ume-wine umes are effective even when they are not pulverized by means of a special pulverizer. But the case that the ume seeds are orally taken after being crunched with the teeth in the mouth is also included in the present invention, although the seeds of the O-ume variety are large, and the outer core of them may be too hard to be crunched with the teeth.

Recently, the pickled umes made of ume fruits of the Ko-ume variety, the seeds of which are of about 2 to 3 mm in the size, are on the market. When eating the pickled umes of the Ko-ume variety, it is naturally included in the present invention, as far as taking the seeds after crunching them with the teeth. In this case, it is preferable to eat about 10 to 20 or more of the pickled umes of the Ko-ume variety a day together with their seeds, since the dry weight of the seeds of the Ko-ume variety is about 0.2 g, and also the sarcocarp of the pickled umes has also therapeutical effect.

Although it remains to be studied in the future why the medicine of the present invention exerts such phenomenal effects, it is considered that the therapeutical effect can be ascribed to remarkable improvement of the blood flow rate or speed after taking the medicine of the present invention.

EXAMPLES

The present invention can be illustrated in the following examples. The present invention, however, is not restricted only to these examples.

Example 1

The seeds of pickled umes originated in pickled-ume factories or ume-wine umes originated in ume-wine factories were collected. The seeds derived from the pickled umes and the ume-wine umes were washed with water, and extraneous matters such as the dusts attached to the surface of the outer core were eliminated. The sarcocarp adhered to the seeds is left behind, because it is not harmful. The cleansed ume seeds, after dried at 60° C., were pulverized with a pulverizer to yield powders of about 100 to 900 $\mu$m in the size.

Example 2

The seeds taken out from the pickled-umes of the O-ume variety produced in Wakayama prefecture were cleansed and dried for 30 hours at 80° C0 with hot air, and pulverized with a pulverizer to yield powders of about 200 to 300 $\mu$m in the size.

Reported Example A

The following reports were given from the diseased subjects among the people who tasted the health foods of the present invention (the pulverized product produced by the example 1).

The subjects with chronic gastric hyperacidity (3 men and 2 women) orally ate 10 g/time of the pulverized product of the example 1, 3 times a day and continued to take it or 6 months. In 20 to 40 minutes after taking, they eructated, and the heaviness feeling in the stomach characteristic to the gastric hyperacidity disappeared. And during the period of about 6 months when they orally took continuously, they happened to have parties several times, and took saccharide and fatty components slightly more than enough. Nevertheless, they did not feel heaviness in the stomach as before having taken the medicine of the present invention.

In the people mentioned above, after having orally taken the medicine of the present invention for about 6 months, the hemodynamic state was improved as compared with that before having taken it, and spots in the skin were decreased. In addition, the present inventor himself also experienced improvement in the hemodynamic state by taking the present medicine, and the spots located in the specific parts of the body disappeared 3 months later after having taken it as above.

Reported Example B

The reports shown in Table 1 to Table 4, were given from the diseased subjects among the people who tasted the health foods of the present invention (the pulverized product in the example 2).

TABLE 1

| Age | Sex | Symptom, Disease | Dosage, Times a day | Duration of taking | Condition after taking |
|---|---|---|---|---|---|
| 43 | Male | Gastric ulcer | 2 g, 3 times | 10 days | Pain disappeared in 2 to 5 minutes after taking each time. Even after 10 days elapsed, he continuously took the present medicine for 3 months, and pain and nausea disappeared. |

TABLE 1-continued

| Age | Sex | Symptom, Disease | Dosage, Times a day | Duration of taking | Condition after taking |
|---|---|---|---|---|---|
| 60 | Female | Stomachache | 2 g on the painful occasion | 8 days | Pain disappeared in 5 minutes after taking the present medicine each time. |
| 45 | Male | Gastric dilatation, Gastric ulcer | 4 g, 3 times | 22 days | Pain and nausea disappeared in 5 minutes after taking the present medicine each time. After taking it for 1 month, the gastric condition normalized. Further, the body weight was decreased by 10 kg in 3 weeks. |
| 65 | Male | Gastric hyperacidity | 4 g, 5 times | 15 days | Pain and nausea disappeared in 2 to 5 minutes after taking the present medicine each time. He could discontinue a common use of other gastric drugs. |
| 30 | Female | Gastric hyperacidity | 2 g, twice | 9 days | Pain and nausea disappeared in 3 to 5 minutes after taking the present medicine each time. |
| 26 | Female | Gastric hyperacidity, Menorrhalgia | 3 g, twice | 10 days | Stomachache disappeared in 5 minutes after taking the present medicine each time. Even after 10 days elapsed, she continuously took it, and pain and heartburn disappeared. Menorrhalgia also disappeared. |
| 30 | Female | Stomachache, Menorrhalgia, Nausea | 2 g, 3 times | 13 days | Pain and nausea disappeared in 2 to 3 minutes after taking the present medicine each time. Menorrhalgia also disappeared. She was relieved from being tired. The body weight was increased by 2 kg. |
| 38 | Male | Gastric hyperacidity, Nausea | 2 g, 3 times | 18 days | Nausea disappeared in 10 minutes after taking the present medicine each time. He was relieved from dyspepsia. |
| 51 | Male | Stomachache, Heartburn | 2 g, twice | 17 days | Pain disappeared in 10 minutes after taking the present medicine each time. Even after 17 days elapsed, he continuously took it, and pain and nausea disappeared. |
| 51 | Female | Heartburn | 2 g, twice | 7 days | She was relieved from nausea. |
| 45 | Male | Stomachache, Heartburn | 4 g, twice | 5 days | Pain and nausea disappeared in 2 to 5 minutes after taking the present medicine each time. He could discontinue taking other gastric drugs. |
| 50 | Female | Stomachache, Heartburn | 4 g, twice | 8 days | Pain disappeared in 5 to 10 minutes after taking the present medicine each time. Even after 8 days elapsed, he continuously took it, and pain and nausea disappeared. |
| 74 | Male | Diabetes mellitus | 4 g, twice | 30 days | The blood sugar level was decreased from 186 to 167 mg/dl. |
| 70 | Female | Stomachache | 2 g, twice | 15 days | Stomachache was alleviated in 20 minutes after taking the present medicine each time. |
| 46 | Male | Arrhythmias | 4 g, 3 times | 27 days | Signs of arrhythmias disappeared. |
| 64 | Male | Gout, Diabetes mellitus | 2 g, twice | 30 days | Pain due to gout was alleviated. The blood sugar level was not increased, even when he drank alcoholic beverages in large quantity. |
| 2 | Female | Atopic disease | 2 g, 5 times | 30 days | Eczema disappeared on the 3rd day after taking the present medicine. In 30 days she was completely cured of atopic disease. |
| 63 | Female | Stiffness in the shoulders | 4 g, twice | 3 days | Stiffness in the shoulders was alleviated. |

TABLE 2

| Age | Sex | Symptom, Disease | Dosage, Times a day | Duration of taking | Condition after taking |
|---|---|---|---|---|---|
| 28 | Female | Stomachache, Cystitis | 6 g, 3 times | 7 days | Stomachache disappeared. She was cured of cystitis, and the frequency of urination was increased. Even after 7 days elapsed, she continuously took the present medicine, and stomachache disappeared. |
| 57 | Male | Prostatic Hypertrophy, Stiffness in the shoulders | 6 g, 3 times | 15 days | Stiffness in the shoulders was alleviated. The frequency of urination was increased. |
| 51 | Female | Insomnia, Stiffness in the shoulders | 6 g, twice | 13 days | She became able to sleep without taking hypnotics. Stiffness in the shoulders disappeared. |
| 56 | Female | Heartburn, Diabetes mellitus | 6 g, twice | 17 days | Dull feeling in the stomach disappeared. The frequency of urination was increased. |
| 65 | Male | Stomachache, Heartburn, Headache | 5 g, twice | 10 days | Headache was remarkably improved. In 10 days, he was completely cured of eczema and stomachache, and heartburn also disappeared. |

TABLE 2-continued

| Age | Sex | Symptom, Disease | Dosage, Times a day | Duration of taking | Condition after taking |
|---|---|---|---|---|---|
| 56 | Male | Diabetes mellitus, Stiffness in the shoulders | 4 g, 3 times | 5 days | Stiffness in the shoulders was alleviated. Symptoms of diabetes mellitus were also improved. |
| 78 | Female | Diabetes mellitus, Cardiac disease | 5 g, 3 times | 180 days | The disease state was improved to the extent that the pace-maker could be removed. Diabetes mellitus was also improved. |
| 37 | Male | Gastric hyperacidity, Atopic disease | 6 g, twice | 15 days | Reflux of the gastric juice stopped. He was almost completely cured of atopic disease. |
| 53 | Male | Gastric ulcer, Insomnia | 4 g, 3 times | 13 days | Dull feeling in the stomach disappeared, and he was relieved from stiffness in the shoulders. He became able to sleep well. |
| 62 | Female | Gastric hyperacidity, Insomnia | 4 g, 3 times | 19 days | Gastric condition got better, and she became able to sleep well. |
| 48 | Female | Duodenal ulcer | 5 g, twice | 8 days | Dull feeling in the stomach disappeared, and stomachache also disappeared. |
| 70 | Male | Heartburn | 4 g, 3 times | 2 days | Nausea disappeared. |
| 62 | Male | Heartburn | 6 g, twice | 3 days | Heartburn disappeared. |
| 33 | Female | Stiffness in the shoulders | 2 g, twice | 5 days | Stiffness in the shoulders disappeared. |
| 36 | Female | Stomachache, Heartburn | 4 g, twice | 10 days | Heartburn and stomachache disappeared immediately after taking the present medicine each time. Even after 10 days elapsed, she continuously took the medicine, and she was relieved from heartburn. |
| 33 | Female | Stomachache, Heartburn | 3 g, twice | 18 days | Stomachache disappeared in 2 to 10 minutes after taking the present medicine each time. Even after 18 days elapsed, she continuously took it, and she was relieved from stomachache and nausea. |
| 60 | Female | Stomachache | 2 g, 3 times | 10 days | Stomachache disappeared within 5 minutes after taking each time. Even after 10 days elapsed, she continuously took the present medicine, and she was relieved from stomachache and nausea. |
| 33 | Female | Gastric ulcer, Stomachache | 4 g, twice | 13 days | Stomachache disappeared in 5 to 10 minutes after taking the present medicine each time. |
| 46 | Female | Hepatitis C | 5 g, 6 times | 45 days | Weariness and fatigue feeling disappeared in 4 to 5 days, and laboratory tests taken in 45 days after taking the present medicine showed normal level. |

TABLE 3

| Age | Sex | Symptom, Disease | Dosage, Times a day | Duration of taking | Condition after taking |
|---|---|---|---|---|---|
| 29 | Female | Atopic disease, Gastric ulcer | 10 g, 4 times | 240 days | She was taken ill at 2 years old. In thirty days after taking the present medicine, body fluid oozed from all over the body, especially, in large quantity from the breast. The body fluid oozed from the body smelled bloody. The body fluid decreased in the quantity as getting odorless, and stopped oozing in 4 months. In 5 months the face became fine, and in 7 months the atopic signs slightly remained only on the back of the hands and fingertips. In 8 months the atopic signs disappeared, and her mother was delighted saying that she did not see such a fine face of her daughter until then. Gastric ulcer was improved in about 10 days after taking. |
| 34 | Male | Atopic disease | 5 g, 4 times | 150 days | In 30 days after taking the present medicine, the body fluid oozed, especially, in large quantity from the nipples. When discontinued taking halfway, oozing of the fluid from the nipples stopped on the next day. On taking again one week later, the body fluid began oozing from the nipples and various parts of the body on the next day. By taking the medicine, materials suspected to be toxins of the atopic disease was excreted from the body. In 5 months after taking, oozing of the fluid from the nipples stopped. Thereafter, |

TABLE 3-continued

| Age | Sex | Symptom, Disease | Dosage, Times a day | Duration of taking | Condition after taking |
|---|---|---|---|---|---|
| | | | | | the inflamed parts of the atopic disease disappeared, and he was almost completely cured of the atopic disease, with leaving the marks of inflammation on the back of the hands. He was released from the atopic disease having suffered him for more than 10 years. |
| 3 | Male | Atopic disease, Infantile asthma | 2 g, 3 times | 22 days | Since he did not try to take the present medicine, it was ingested being mixed in rice-balls. He was almost completely cured of the atopic disease, and asthma attacks stopped coincidentally. |
| 2 | Male | Atopic disease | 2 g, 3 times | 21 days | Since he did not try to take the present medicine, it was ingested being mixed in rice-balls. And he was almost completely cured of the disease. |
| 2 months | Female | Atopic disease | 3 g, 14 times (mother) | 4 days | Since she was too young to take the present medicine, her mother took it instead. She took her mother's milk. The infant was cured of the disease in 4 days, suggesting that her mother's milk got well. |
| 2 | Male | Atopic disease | 3 g, 3 times | 15 days | He was cured almost completely of the atopic disease. |
| 2 | Female | Atopic disease | 5 g, twice | 4 days | The disease condition was considerably severe. When the present medicine was given as much as she requested from 2 days before the prearranged hospitalization, the symptoms were rapidly improved, and she was cured of the disease in 4 days. |
| 2 | Male | Atopic disease | 2 g, 3 times | 30 days | He was almost completely cured of the disease. |
| 2 | Male | Atopic disease | 3 g, 3 times | 12 days | He was almost completely cured of the disease. |
| 2 | Female | Atopic disease | 2 g, 3 times | 14 days | She was almost completely cured of the disease. |
| 3 | Male | Infantile asthma | 3 g, 3 times | 15 days | He was almost completely cured of the disease. |

TABLE 4

| Age | Sex | Symptom, Disease | Dosage, Times a day | Duration of taking | Condition after taking |
|---|---|---|---|---|---|
| 62 | Female | Ovarian cancer, Stiffness in the shoulders | 3 g, 10 time | 60 days | In about 30 days after taking the present medicine, the tumor of 4 cm in the size was divided into 2 parts of 2 cm and 1 cm. In 60 days the cancer almost completely disappeared. |
| 58 | Male | Leukemia | 10 g, 4 times | 240 days | The number of leukocyte was decreased from 5,500 to 3,000 to 3,500, and stabilized. The chief physician commented that it was rare to be improved to such a level. |
| 63 | Female | Stomach cancer | 3 g, 3 times | 1.5 years | She started taking the present medicine about 5 months after surgical operation of *Scirrhous carcinoma* of the stomach. One year later, operation was performed again, but no metastasis was found. The chief physician said that she was lucky without metastasis. Thereafter, the dosage was increased. |
| 52 | Female | Gastric polyps, Arrhythmias | 10 g, 5 times | 60 days | Pain having lasted for 2 months disappeared soon after taking the present medicine. One month later, the polyps also disappeared. No relapse of arrhythmias has occurred after taking the medicine. |
| 60 | Female | Polyps of the colon intestine | 10 g, 8 times | 15 days | On the checkup taken 2 weeks after taking the present medicine, it was found that the polyps completely disappeared. |
| 51 | Female | Polyps of the colon intestine | 10 g, 5 times | 15 days | On the checkup taken 15 days after taking the present medicine, it was found that the polyps disappeared. |
| 58 | Male | Myocardial infarction, Stiffness in the shoulders | 15 g, 4 times | 11 months | He had heart attacks about twice every month, but during 11 months when he took the present medicine, no attack has occurred. Stiffness in the shoulders also disappeared. |
| 48 | Male | Arrhythmias | 10 g, 5 times | 35 days | He had arrhythmias occasionally, but he has no arrhythmias after taking the present medicine. |
| 36 | Female | Pollinosis | 10 g, 8 times | 90 days | Symptoms of pollinosis disappeared. She was also almost completely cured of rhinitis from which she suffered for a long time. |

TABLE 4-continued

| Age | Sex | Symptom, Disease | Dosage, Times a day | Duration of taking | Condition after taking |
|---|---|---|---|---|---|
| 60 | Female | Pollinosis, Stiffness in the shoulders | 10 g, 5 times | 120 days | Symptoms of pollinosis disappeared. Stiffness in the shoulders also disappeared. |
| 55 | Female | Stiffness in the shoulders, Spots | 2 g, 5 times | 90 days | Stiffness in the shoulders disappeared immediately, and spots in the skin disappeared in about 3 months. |
| 28 | Female | Stiffness in the shoulders, Spots | 3 g, 5 times | 180 days | Stiffness in the shoulders disappeared immediately, and spots in the skin disappeared unawares. |
| 64 | Male | Spots | 10 g, 6 times | 180 days | Spots in the skin rapidly became faint. He got to be hardly tired. |
| 66 | Male | Pollinosis, Stiffness in the shoulders, Spots, Gastric ulcer | 15 g, 6 times | 120 days | Spots in the skin of the hands completely disappeared in 3 months. He was almost completely cured of pollinosis which he had experienced every year. Stiffness in the shoulders disappeared. It became unnecessary to take gastric drugs of which he had to take 10 tablets or more a month. |
| 28 | Female | Hypo-thyroidism | 10 g, 6 times | 1 year | She was told by a doctor that she had to take western drugs all through her life. However, in 3 months after taking the present medicine the condition became very well. Thus, all the hormone drugs were withdrawn, and she takes no drugs other than the medicine of the present invention. |

INDUSTRIAL APPLICABILITY

As mentioned above, the ume seeds (for example, the seeds derived from pickled ume, and the seeds derived from ume-wine ume), which were industrial waste, can be reused as medicines for prevention of or treatment for various diseases through simple production processes including cleansing, drying and pulverizing.

What is claimed is:

1. A health food or drink, comprising a pulverized product of ume seed, wherein the ume seed comprises the outer core, endocarp and embryo, wherein the ume seed is obtained from Prunus Mume Sieb, et Zucc., and wherein the pulverized product has a particle diameter of or 100 to 900 µm, or wherein the pulverized product passes through a 30 to 150 mesh filter.

2. The health food or drink according to claim 1, wherein the ume seed is obtained from pickled ume or ume-wine ume.

3. The health food or drink according to claim 1, wherein the pulverized product of the ume seed is obtained by pulverizing the seed obtained from pickled ume or the seed obtained from ume-wine ume.

4. The health food or drink according to claim 1, which is in the form of a powder, tablet, granule or capsule.

5. A medicine, comprising a pulverized product of ume seed, wherein the ume seed comprises the outer core, endocarp and embryo, wherein the ume seed is obtained from Prunus Mume Sieb, Zucc., and wherein the pulverized product has a particle diameter of or 100 to 900 µm, or wherein the pulverized product passes through a 30 to 150 mesh filter.

6. The medicine according to claim 5, wherein the ume seed is obtained from pickled ume or ume-wine ume.

7. The medicine according to claim 5, wherein the pulverized product of the ume seed is obtained by pulverizing the seed obtained from pickled ume or the seed obtained from ume-wine ume.

8. The medicine according to claim 5, which is in the form of a powder, tablet, granule or capsule.

9. A method for treating gastric hyperacidity, a stomachache or heartburn, which comprises administering a therapeutically effective amount of a pulverized product of ume seed, wherein the ume seed comprises the outer core, endocarp and embryo, wherein the ume seed is obtained from Prunus Mume Sieb at Zucc, and wherein the pulverized product has a particle diameter of 100 to 900 µm, or wherein the pulverized product passes through 30 to 150 mesh filter, to a patient in need thereof.

* * * * *